United States Patent [19]

Klein et al.

[11] Patent Number: 4,571,242
[45] Date of Patent: Feb. 18, 1986

[54] TAMPER PROOF CAP FOR SYRINGES AND THE LIKE

[75] Inventors: Richard B. Klein, Warren; William S. Scavuzzo, Clark, both of N.J.

[73] Assignee: C. R. Bard, Inc., N.J.

[21] Appl. No.: 622,215

[22] Filed: Jun. 19, 1984

[51] Int. Cl.⁴ .............................................. A61M 5/00
[52] U.S. Cl. .................................. 604/111; 604/187; 220/306
[58] Field of Search ...................... 604/111, 187, 110; 220/306, 307; 206/364

[56] References Cited

U.S. PATENT DOCUMENTS 3,994,412  11/1976  Difiglio ........................... 604/111 X
4,286,591  9/1981  Raines ................................. 604/187

*Primary Examiner*—Stephen C. Pellegrino
*Attorney, Agent, or Firm*—Kane, Dalsimer, Kane, Sullivan and Kurucz

[57] ABSTRACT

This invention pertains to a tamper-proof sealing cap for a syringe. The cap is made of a partially rubber-like flexible material so that it may be partially deformed from its preselected shape. At least one of its members is preformed into a shape which prevents the re-insertion of the syringe after it has been removed.

21 Claims, 16 Drawing Figures

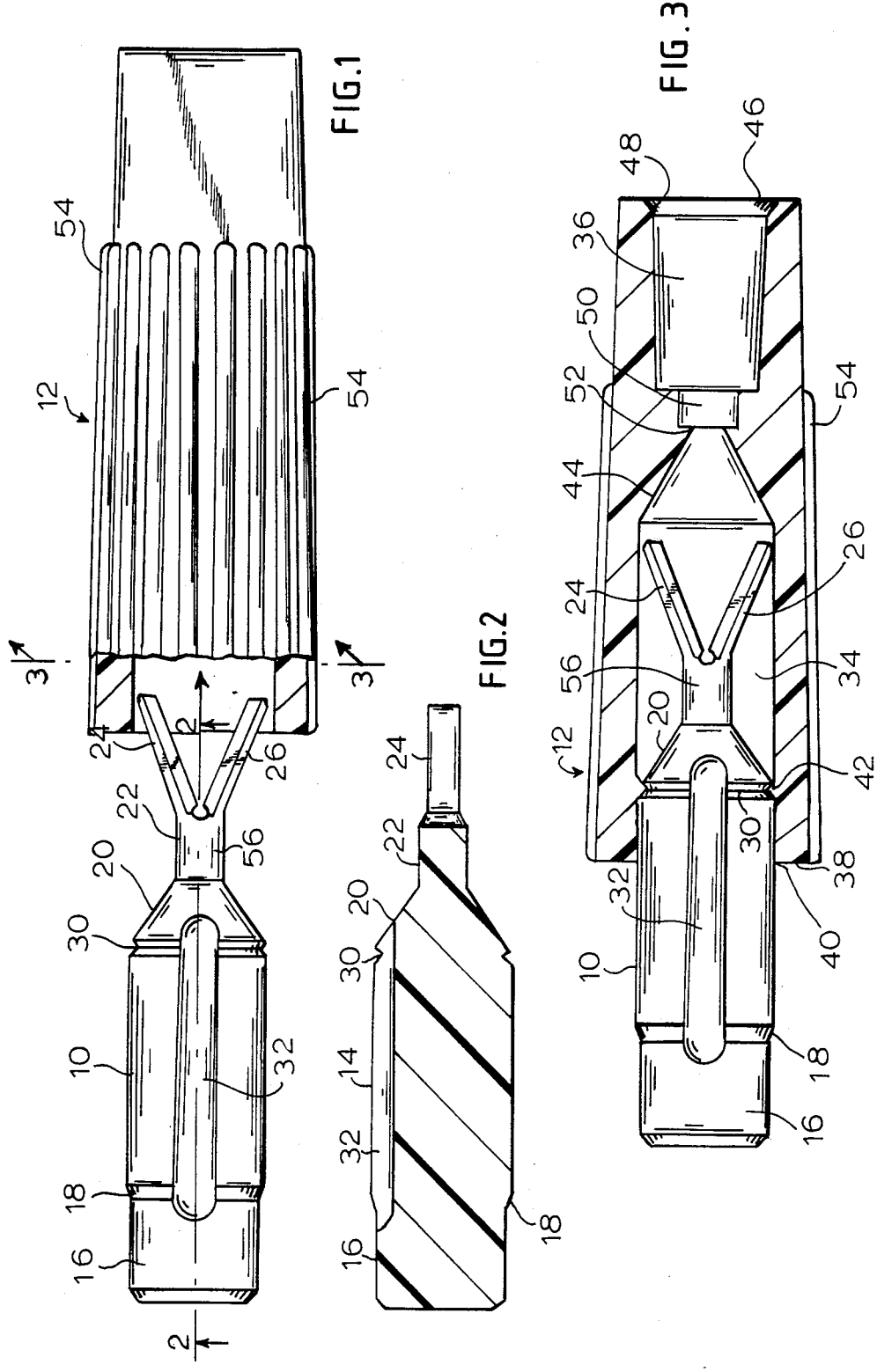

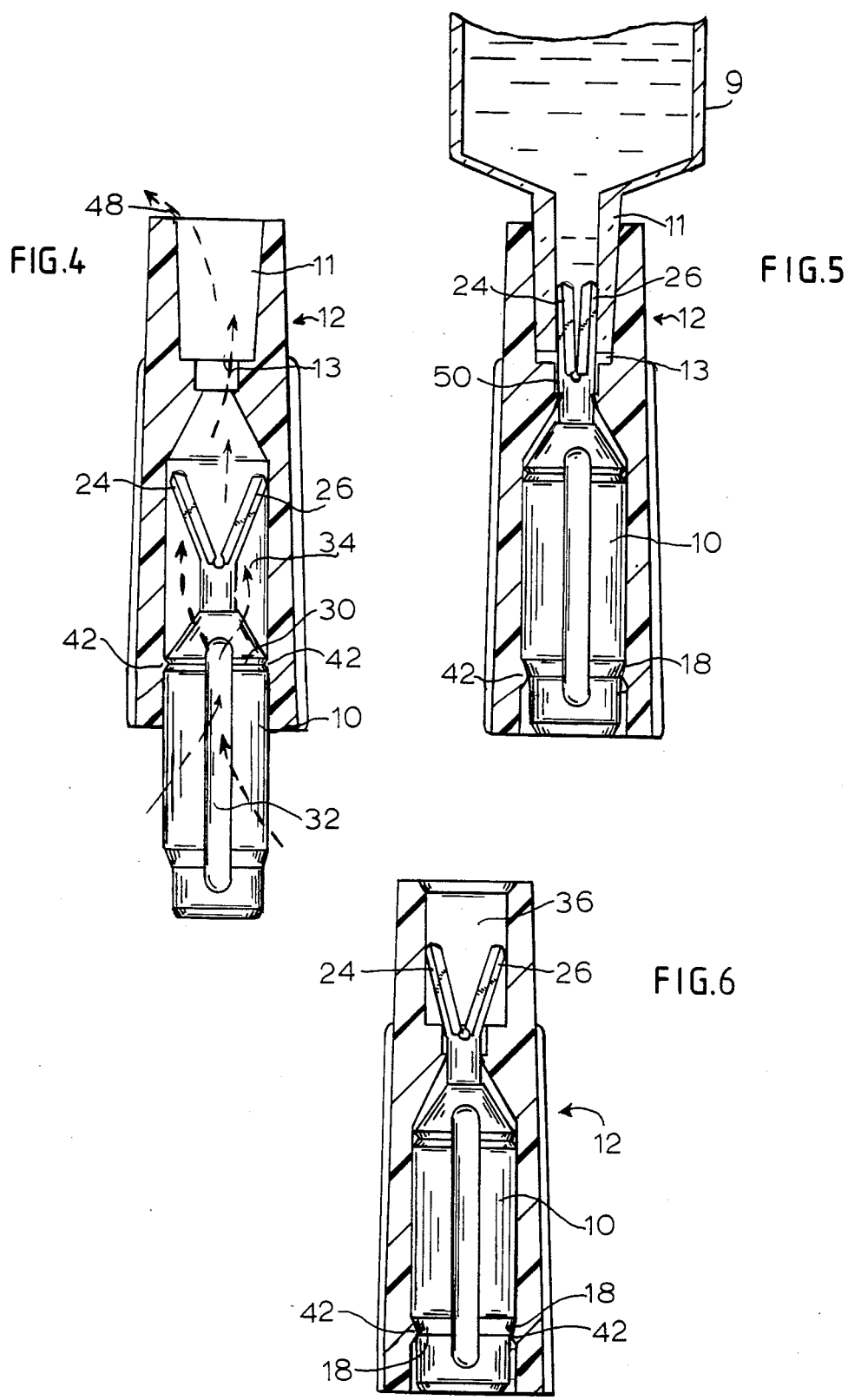

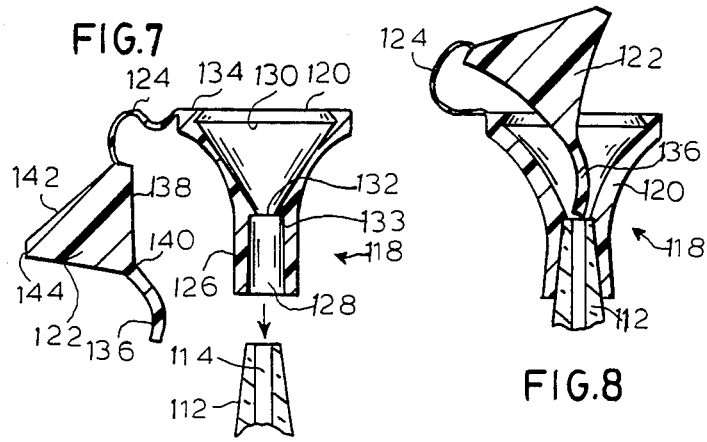
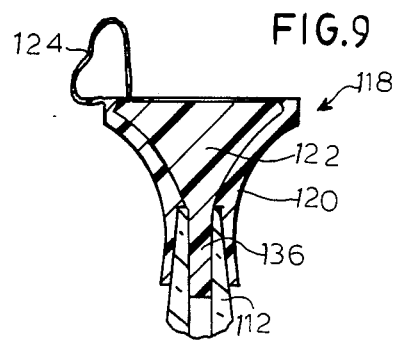
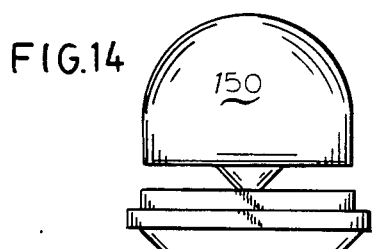
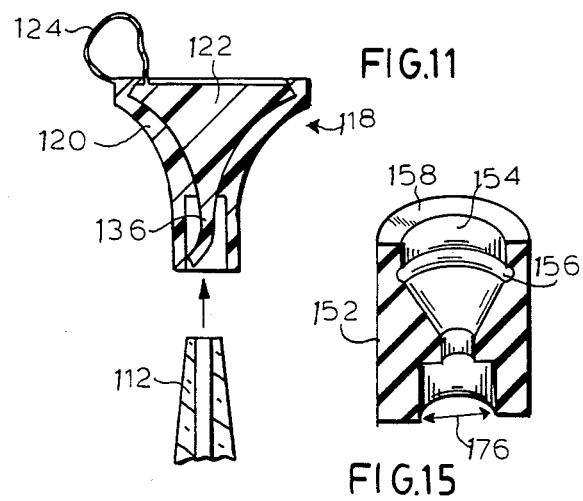
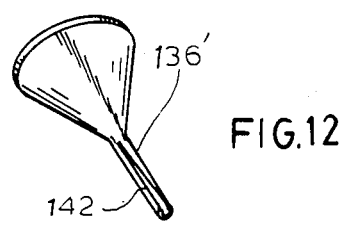
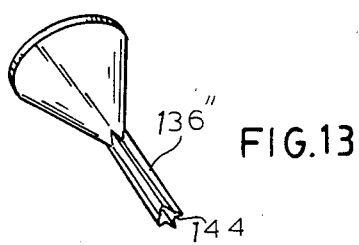
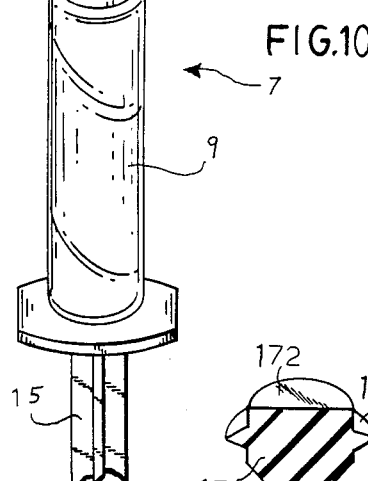
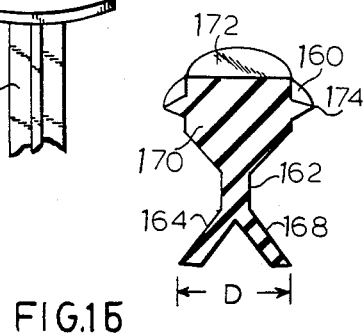

TAMPER PROOF CAP FOR SYRINGES AND THE LIKE

DESCRIPTION OF THE PRIOR ART

1. Field of Invention

This invention pertains to a cap for a dispenser such as a syringe with means for indicating tampering of said dispenser.

2. Description of the Prior Art

Disposable syringes have become very popular in the health care field. Such syringes have a number of advantages over standard syringes. Since they are used only once they can be made relatively cheaply of plastic materials, and with plungers which don't require close tolerances.

It has been further found to be advantageous to fill the disposable syringes with an appropriate substance at the site where the substance is manufactured or distributed. Using prefilled syringes leads to savings of time, space and inventory and generally a cleaner, more antiseptic procedure since the medicine or other substance contained in the syringe is dispensed directly without the necessity of removing the medicine from another, possibly contaminated container. Furthermore each syringe can be clearly labelled according to its contents and/or intended use.

However between the time that the syringe is filled and the time its contents are removed the syringe must be sealed so that its contents do not spoil, spill etc. Furthermore a need arose for a sealing means which also indicated tampering of a syringe, i.e. removal of or changing its contents.

OBJECTIVES AND ADVANTAGES OF THE INVENTION

An objective of the present invention is to provide a sealing means for prefilled syringes and similar articles.

Another objective is to provide a sealing means with tamper-proof indication.

A further objective is to provide a single sealing means which is easy and inexpensive to manufacture.

Yet another objective is to provide sealing means which also facilitates filling the syringe. Other objectives and advantages shall become apparent in the following description of the invention.

According to the present invention a cap for syringe comprises a tubular member which fits over the mouth of the syringe and a plug which fits snugly inside tubular member. The plug is pre-formed to a shape which is different from its configuration while it is disposed within at the tip of a syringe. When the cap is removed from the syringe the plug assumes its original shape preventing reclosure of the syringe.

BRIEF DESCRIPTION OF THE DRAWINGS

FIG. 1 illustrates the preferred embodiment of the invention;

FIG. 2 shows a sectional view of one of the elements of the preferred embodiment;

FIG. 3 shows the two elements of the invention in an intermediate configuration;

FIG. 4 shows the invention being sterilized;

FIG. 5 shows the invention in sealed position attached to a filled syringe; FIG. 6 shows the invention after detachment from the syringe;

FIGS. 7–11 show details of a second embodiment of the invention;

FIG. 12 shows a third embodiment of the invention;

FIG. 13 shows a fourth embodiment of the invention; and

FIG. 14–16 show details of a fifth embodiment of the invention.

DETAILED DESCRIPTION OF THE INVENTION

As shown in FIG. 10, a typical disposable syringe 7 comprises a cylindrical body 9 which tapers to a rather narrow tip 11 with a circular orifice 13. At the end opposite tip 11, a plunger 15 is provided for dispensing the contents of the syringe.

The preferred embodiment shown in FIGS. 1, 2 and 3 comprises two elements: a plug 10 and a tubular member or sleeve 12. The plug has a rather-bullet shaped or cylindrical main body 14. At one end 16 the body is slightly reduced in diameter. Between end 16 and the main body 14 of the cap there is an annular shoulder 18. The opposite end of the body is connical as at 20 and terminated in a rod 22 axially oriented with main body 14. The rod is terminated by two legs 24 and 26 which are co-planar with each other and which are oriented at an acute angle with respect to the longitudinal axis of the main body as shown. Between main body 14 and connical end 20 there is an annular depression 30. A generally elongated depression 32 is also formed on the plug which extends longitudinally substantially along the length of the plug from connical end 20 to end 16.

Preferably the plug 10 molded of a soft plastic material of the kind which is very flexible and which deforms permanently if excessive force is applied to it.

The tubular member 12, as shown in FIG. 3 is made with two axially spaced cylindrical cavities 34 and 36. The longitudinal cross-sectional shape and size of the first cavity 34 is generally complementary to the main body 14 and the two ends 16 and 20 of plug 10. At one end the cavity starts with an opening 40 and axially spaced from said opening a bead 42 is provided to form an orifice having a diameter which is smaller the diameter of main body 14. Cavity 34 ends in a connical section 44 which is generally complementary to end 20.

Cavity 36 starts at the end 46 opposite end 38 with a slightly enlarged opening 48. Between cavities 36 and 34 there is a communicating channel 50 which ends in an annular shoulder 52. The inner diameter of this shoulder is preferably slightly smaller than the diameter of rod 22.

Sleeve 12 is provided with a plurality of longitudinal ribs 54 which are essentially coextensive with the first cavity 34. Sleeve 12 and plug 10 may be made by molding from a relatively rigid plastic material. Preferably sleeve 12 is made of a relatively transparent or translucent material so that the inner cavities 34 and 36 are clearly visible. The outer surface of the sleeve 12 covered by ribs 54 may be texturized while the remaining part should be left clear. Preferably plug 10 should be brightly colored so that the position and orientation of the rod 22 and the two legs is clearly visible through the sleeve.

The closure of FIGS. 1–6 is used as follows. After elements 10 and 12 are manufactured, they are preassembled by inserting end 20 of the plug into cavity 34 until bead 42 engages depression 30 as shown in FIG. 3. In this intermediate configuration the closure is easy to pack and ship. The interlocking between the two elements insures that they do not separate. Furthermore the positive locking between the elements permits a rapid and easy pre-assembly of the closure. This pre-assembly requires virtually no skills or experience and may even be performed by blind persons.

Preferably, prior to shipping, the closure is sterilized by blowing through it an antiseptic gas such as ethyl oxide (ETO). As shown in FIG. 4, this gas may be blown through depression 32, cavity 34, cavity 36 and out through opening 48.

In the configuration shown in FIGS. 3 or 4 the closure may be readily attached to, and removed from a syringe because the cavity 36 is dimensioned to form an interference fit with syringe tips 11. Thus the closure may be shipped to a filling location either by itself, or mounted on a syringe.

After the syringe is filled with an appropriate fluid, the closure is placed on the syringe and then is closed to its second position by pushing plug 10 forward all the way into the sleeve. As the plug moves into the sleeve, toward its final positon (see FIG. 5), legs 24 and 26 are forced toward each other so that by the time they reach shoulder 52 they are adjacent to each other. The legs are maintained in this adjacent position by the shoulder 52 so that they slip easily into syringe orifice 13 of the syringe tip 11 as shown.

During the forward movement of the plug within the sleeve, the sleeve is slightly deformed at end 38 because, as previously described, the opening defined by 42 is smaller than the diameter of plug main body 14. As soon as narrower end 16 reaches bead 42 the sleeve snaps back to its original, non-deformed configuration, thus capturing the plug. In this position rod 22 mates with shoulder 52 to provide a final seal for the syringe. Effectively, a first seal is provided between the outer wall of syringe tip 11 and the inner wall of cavity 36, and a second seal is provided by the shoulder 52 and rod 22. It should also be noted that some syringes are also provided with an outer ring surrounding the syringe tip. Usually the inner surface of said outer ring is threaded so that an appropriate nozzle could be attached to the syringe. For this type of syringe, the sleeve may be shaped and dimensioned so a portion of its outer wall forms a seal with the inner wall of said syringe ring.

Before the contents of the syringe are dispensed the closure is removed therefrom. Since the plug 10 is still captured by the sleeve 12, as shown in FIG. 6, removal from the syringe allows legs 24 and 26 to separate until they come in contact with the walls of cavity 36. In this configuration the closure cannot be replaced on a syringe tip because the tip will merely bend legs 24, 26 out of shape. Furthermore any excessive force will permanently deform the legs so that the closure could not be reused. Thus once the plug 10 is fully plunged into tube 12 the closure may not be placed on a syringe. In the configuration of FIG. 6 the plug 10 and sleeve 12 can be separated only by using a sharp instrument which would permanently damage or deform the plug and/or the sleeve thereby providing an indication that the closure was forced. Throughout the closing and opening process the status and position of the plug and its brightly colored legs may be visually monitored through the transparent sleeve.

In an alternate embodiment of the invention, a cap 118 (FIG. 7) comprises a tubular member 120 and a plug 122 which are connected together by tether 124. Since the tip of the syringe, and therefore the actual size of the cap is relatively small, tether 124 is provided to insure that the plug 122 is not lost, misplaced or contaminated while the syringe is being filled.

The tubular member comprises two portions. The first portion 126 is substantially cylindrical and is provided with an inner cavity 128. The second portion 130 is in the shape of funnel, or connical, with a relative large opening 130 at one end, and a smaller opening 132 at the other. The two portions are disposed so that the smaller opening 132 is adjacent to cavity 128 as shown. The diameter of cavity 128 is slightly larger then opening 132 so that shoulder 133 is formed at the interface between the two portions. The whole member 118 is formed as a single piece by well-known techniques out of a plastic or rubber material. The larger opening 130 is chamfered slightly inward as shown, by lip 134.

Plug 122 also comprises two portions 136 and 138. The first portion 136 is in the shape of a rod. As shown in FIG. 6, portion 136 is preformed into the shape of the letter J. Portion 138 has a truncated frustoconnical shape which is joined at its narrower end 140 to first portion 136. Preferably the top, wider end 142 of portion 138 is terminated by a slanted surface 144 which narrows it slightly.

The cap is used as follows. First tubular member 120 is installed on an empty syringe, as shown on FIGS. 7 and 8, so that tip 112 is pushed into member 120 until it abuts shoulder 133. In this configuration, tubular member forms a perfect funnel through which the syringe can be filled up with the desired drug or other substance. For this purpose opening 130 is much larger than orifice 114 on the syringe and the tip is sealed by tubular member except the orifice 132 which allows entry into the syringe. Thus the syringe could be filled up with relative ease by placing an appropriate dispensing nozzle in or adjacent to the second portion 130 of the tubular member 120. The dispensing nozzle could be a part of an automatic syringe-filling apparatus well-known in the art.

Once the syringe is filled to the proper level, it is ready to be sealed. The tubular member is dimensioned so that as the tip inserted into cavity 128 an interference fit is created therebetween, and therefore the tubular member will not fall off the syringe unless it is pushed off by an external means. The syringe is sealed by inserting plug 122 into tubular member 120, as shown in FIGS. 8 and 9, through the top, or funnel portion 130. In the final position of FIG. 9 rod-shaped portion 136 is disposed within the orifice 114 of the syringe and the second portion 138 is disposed within and captured by the funnel-shaped portion 130 of the tabular member. It can be seen that the plug 122 has the same shape, or is slightly larger than the voids of tubular members 120 so that when it is inserted in said voids it substantially fills it up and an interference fit is formed between the two members of the the cap.

Furthermore rod 136 has a diameter which is equal to or slightly larger than syringe orifice 114 so that it forms an effective cork. Thus the frictional forces between the tubular member, the tip of the syringe and the plug insure that the syringe is properly sealed and that the the cap is securely affixed to the syringe.

Before an appropriate nozzle is attached to the syringe cap is removed as shown in FIGS. 10 and 11. Since the overall diameter of the cap is larger than the diameter of the syringe tip, the cap is relatively easy to pry off by hand. Once the cap is removed, rod 136 goes back to its original J shape as shown in FIG. 11. Preferably the rod is sufficiently curved so that, once the cap is removed, rod 136 abuts or comes in contact with the sidewalls of cavity 128. Therefore, once the cap is removed, the rod will prevent its reinsertion on to the syringe by blocking cavity 128. Furthermore lip 134 on the top of tubular member 130 cooperates with slanted surface 142 to capture the plug. Any attempt to remove the plug 122 from the tubular member 120 causes a deformation of lip 134 and/or the plug thereby providing clear visual evidence of tampering.

The cap may be made of any plastic or rubber material by standard molding techniques. Furthermore the caps could be color-coded in accordance with intended use of the drug contained in the syringe.

Three other embodiments for the enclosure are shown in FIGS. 12, 13 and 14. In FIG. 12 member 136' is tubular and is formed with a longitudinal slit 142. In this form the member 136' has an outer diameter which is larger than the syringe orifice 114 so that once the cap is withdrawn the member 136' is too large to be reinserted.

In the embodiment of FIG. 13 member 136" is provided with a plurality of vanes 144 which also make it impossible to re-use the cap.

In the embodiment of FIG. 14 the plug comprises a stem 144 with two legs 146 and 148 which are preformed to form an angle of about 45° as shown. The two ends can be pushed together to form with stem 144 a continuous rod for engaging and sealing the syringe tip. When the cap is removed the two legs 146, 148 separate and engage the sidewalls of cavity 128. A removable tab 150 is provided on top of the plug which can be used to hold the plug while it is being inserted into the tubular member and syringe tip.

It should be appreciated that in the embodiments of FIGS. 1, 12, 13 and 14 the narrow neck defined by shoulder 133 squeezes rod 136', 136" or ends 146, 148 transversally so that it may fit into the syringe 112. After the cup is removed, the rod or ends expand so that it no longer fits through orifice 114.

Yet another embodiment of the invention is shown in FIGS. 14 and 15. The tubular member 152 has an essentially uniform outer circumference along its length, and has an upper cylindrical cavity 154 with a circumferential groove 156 provided somewhat below the upper surface 158 of the member. The bottom portion of the member is essentially identical to the embodiment of FIG. 7.

Plug 160 (see FIG. 16) has a lower portion 162 comprising a stem 164 and two legs 166 and 168. The top portion 170 of the plug is essentially cylindrical and has a relatively flat top surface 172. Below this surface the top portion has circumferential bead 174. When the tubular member 152 is positoned on a syringe with its tip extending into cavity 176, and the plug is inserted through top cavity 154, the two legs 164, 168 are squeezed together and engage the inner surface of the syringe tip. The bead 174 is provided to engage groove 156. Once the plug is inserted into the tubular member the closure elements 158 and 160 are interlocked through the bead and groove so they cannot be separated therefrom without deforming either or both the tubular member and the plug. Once the cap is removed from the syringe the ends 164, 168 come into contact with the side walls of cavity 176 and the cap cannot be re-used.

Obviously numerous modifications may be made to the invention without departing from its scope as defined in the appended claims.

I claim:

1. A tamper-proof closure for a syringe comprising:
   a tubular member having a first orifice for receiving a syringe tip and a second orifice communicating with said first orifice;
   a plug with a first portion having a first configuration in which said first portion prevents a syringe tip from being inserted into said first orifice when said first portion is in said first orifice and further cooperates with said member to trap said plug when said plug is disposed in said second orifice with said first portion extending into said first orifice; said plug being deformable to a second configuration for sealing said syringe tip, said tubular member being constructed and arranged to deform said first portion into a sealing engagement with said syringe tip as said plug is introduced into said second orifice.

2. The closure of claim 1 further comprising means of interlocking said tubular member and plug so that they cannot be separated without deformation.

3. The closure of claim 2 wherein said tubular member is cylindrical.

4. The closure of claim 2 wherein said second orifice is cylindrical and has a circumferential inner bead, and said plug has a second portion connected to said first portion, said second portion being cylindrical and having an outer circumferential bead, said circumferential bead and bead being arranged to interlock when said plug is inserted in said tubular member.

5. The closure of claim 4 wherein said first portion comprises a stem with two bifurcated flexible legs.

6. The closure of claim 5 wherein said legs have distal ends which are separating a distance which is larger than the diameter of said first orifice of said tubular member.

7. The closure of claim 2 wherein said second orifice is funnel-shaped to facilitate filling the syringe after its tip has been inserted in said first orifice.

8. The closure of claim 7 wherein said first portion comprises a rod.

9. The closure of claim 8 wherein said rod is pre-shaped in a J-shape.

10. The closure of claim 7 wherein the first portion comprises a tubular split member.

11. The closure of claim 7 wherein said first portion comprises a rod with a plurality of vanes.

12. The closure of claim 7 wherein said second orifice has a circumferential lip for capturing said plug.

13. The closure of claim 1 further comprising a tether between said tubular member and said plug.

14. A tamper evident closure for a syringe tip comprising:
   a tubular member having a first cavity disposed and arranged to allow the closure to be secured to said syringe tip; a second cavity communicating with said first cavity;
   a plug having a cylindrical body and a deformable element said element having a first configuration in which said element prevents said syringe tip from being inserted into said first cavity and further cooperates with said member to trap said plug when said plug is disposed in said second cavity with said element extending into said first cavity; said plug being deformable to a second configuration for sealing said syringe tip, said tubular member being constructed and aranged to deform said first portion to said second configuration and direct said first portion into a sealing engagement with said syringe tip as said plug is introduced into said second orifice.

coupling means for holding said plug in a first position in which said plug is removable disposed in said second cavity, and in a second position in which said plug has its deformable element disposed within said first cavity, said plug being removable from said sleeve only be permanently deforming one of said sleeve and plug.

15. The closure of claim 14 wherein said coupling means comprises a groove disposed on said plug opposite to said deformable member and a circumferential bead disposed in said second cavity.

16. The closure of claim 15 wherein said circumferential bead is disposed adjacent to an opening of said second cavity and said plug has a circumferential depression disposed opposite said circumferential groove, said bead and depression cooperating to hold said plug in said second position.

17. The closure of claim 15 wherein said deformable member is adapted to form a seal with said tubular member in said second position.

18. The closure of claim 15 wherein said plug has a longitudinal depression which allows gas to flow through said first and second cavities while said plug is in said first position and permits trapped air to exhaust when the plug is shifted to the second position.

19. The closure of claim 14 wherein said tubular member is transparent and said plug is colored whereby said end is observable while it is inside said tubular member.

20. A tamper-proof sealed syringe comprising:
a dispenser body terminating in a tip with a narrow orifice and adapted to hold and dispense liquids through said orifice;
a liquid contained in said dispenser;
and a sealing cap comprising a tubular body which forms an interference fit with said tip; and a plug disposed within said tubular body, and provided to seal said orifice, said plug having a preselected shape, and being deformed from said preselected shape as it is disposed within said tubular member and tip, said shape being selected so as to prevent the reinsertion of said tip into said tubular body after said cap is removed therefrom.

21. The syringe of claim 20 further comprising means for interlocking the cap and tubular member thereby providing an indication of tampering.

* * * * *

UNITED STATES PATENT AND TRADEMARK OFFICE
CERTIFICATE OF CORRECTION

PATENT NO. : 4,571,242
DATED : February 18, 1986
INVENTOR(S) : Richard B. Klein and William S. Scavuzzo It is certified that error appears in the above-identified patent and that said Letters Patent is hereby corrected as shown below:

In Column 6, line 26, "circumferential bead" should be

--circumferential groove--;

In Column 6, line 27, "bead" (second occurrence) should be

--groove--.

Signed and Sealed this

Seventh Day of April, 1987

Attest:

DONALD J. QUIGG

Attesting Officer

Commissioner of Patents and Trademarks